US012723956B2

(12) United States Patent
Postrel

(10) Patent No.: US 12,723,956 B2
(45) Date of Patent: Sep. 1, 2026

(54) INSTANT NON-INVASIVE HIGH-THROUGHPUT DISEASE SCREENING

(71) Applicant: Richard Postrel, Miami Beach, FL (US)

(72) Inventor: Richard Postrel, Miami Beach, FL (US)

( * ) Notice: Subject to any disclaimer, the term of this patent is extended or adjusted under 35 U.S.C. 154(b) by 274 days.

(21) Appl. No.: 18/670,067

(22) Filed: May 21, 2024

(65) Prior Publication Data

US 2024/0426722 A1 Dec. 26, 2024

Related U.S. Application Data

(63) Continuation-in-part of application No. 18/542,582, filed on Dec. 15, 2023, which is a continuation of application No. PCT/US2022/033697, filed on Jun. 15, 2022, and a continuation-in-part of application No. 17/609,165, filed as application No. PCT/US2021/044852 on Aug. 5, 2021, now Pat. No. 11,988,660.

(60) Provisional application No. 63/210,938, filed on Jun. 15, 2021, provisional application No. 63/190,573, filed on May 19, 2021, provisional application No. 63/061,159, filed on Aug. 4, 2020.

(51) Int. Cl.

| | |
|---|---|
| ***G01N 1/44*** | (2006.01) |
| ***G01N 30/02*** | (2006.01) |
| ***G01N 30/12*** | (2006.01) |
| ***G01N 33/00*** | (2006.01) |

(52) U.S. Cl.

CPC ............... *G01N 1/44* (2013.01); *G01N 30/12* (2013.01); *G01N 33/0016* (2013.01); *G01N 33/0047* (2013.01); *G01N 2030/025* (2013.01); *G01N 2030/128* (2013.01)

(58) Field of Classification Search

None

See application file for complete search history.

(56) References Cited

U.S. PATENT DOCUMENTS

| | | | | |
|---|---|---|---|---|
| 10,935,513 | B2 * | 3/2021 | Liu | G01N 33/48707 |
| 11,988,660 | B2 * | 5/2024 | Postrel | G01N 33/497 |
| 2013/0061660 | A1 * | 3/2013 | Kasama | G01N 27/226 73/31.06 |

FOREIGN PATENT DOCUMENTS

| | | | | |
|---|---|---|---|---|
| CN | 107764806 A | * | 3/2018 | G01N 21/766 |

* cited by examiner

*Primary Examiner* — Peter J Macchiarolo
*Assistant Examiner* — Jermaine L Jenkins

(57) ABSTRACT

A real-time disease detection system that rapidly assesses volatile organic compounds (VOCs). This invention delivers high-sensitivity capture, classification and pattern recognition to identify unique VOC profiles derived from a biosample or gas emitted from a donor (palm). The detector unit can be configured to screen for one or more disease(s), e.g., infectious, autoimmune, oncolytic disease, etc. The sample may be instantly analyzed on-site or collected remotely, thus providing a practical real-time screening process for testing persons of interest, in high-volume, high-throughput, access controlled environments such as airports, convention centers, government facilities, sporting arenas, etc., or examination room, waiting room, remote laboratory, etc. The device can be programmed to screen for a specific disease or for general detection of a plurality of known diseases.

20 Claims, 6 Drawing Sheets

GROUP 61
20
21
17
17
17
17
GROUP 62
17
17
17
17
GROUP 63
-
+
17
17
17
17
2V
2V
3V
3V

INSTANT NON-INVASIVE HIGH-THROUGHPUT DISEASE SCREENING

The present invention is designed for two critical missions-public health and personal health. For public health, the high throughput screening rapidly identifies individuals who present a health risk to the general population from entering a public venue. For personal health, the rapid, reagent-free screening can provide pre-symptomatic detection of infectious diseases or cancers allowing for early treatment that improves patient outcomes.

The rapid, almost instantaneous, identification of disease carriers, permits venues and any commercial establishment to continue to operate safely when experiencing a pandemic or regional infection event. In short, this device if widely disbursed will allow commerce to continue. The device in conjunction with other mitigation strategies such as vaccinations reduces health risks and economic disruption. The device is especially useful when applied at airports, conventions centers, hospitals, schools, stadiums, sporting events, music venues, train stations, courtrooms, office buildings, political rallies, restaurants, bars, retail establishments, etc., i.e., places where groups or crowds gather raising concerns relating to the spread of infectious disease. The process uses no consumables, e.g., chemical reagents, and therefore is capable of non-stop screening large groups of individuals. The process is designed to be more rapid than the screenings common at airports.

To accomplish this, the present invention provides a device and process for assaying volatile organic compounds (VOCs) in a gaseous state from a non-invasive bio-sample. The invention further provides a device that optimizes the capture, classification and pattern recognition necessary for identifying a unique VOC signature derived from that bio-sample. The preferred device can be fitted with features that may include a baton shaped shaft designed to be positioned near the axilla or armpit, an arm that may be extended into, for example, a car window. The device may also be used to screen a collected group of individuals, such as the group of passengers in a car. The entire group, having been confined in proximity to one another may be considered as posing a risk to non-infected individuals.

By assaying VOCs in real time, this invention provides a practical screening device for clearing persons of interest, e.g., in a waiting room, planning to enter a building, a parking lot, a sports venue, or lined up for transit, etc. By measuring and analyzing VOCs emitted onto the skin or through clothing, this invention enables quick and accurate analysis for recognition of bio-threats and/or diseases. The invention can also be used in a hospital, urgent care, or other medical setting to screen patients and visitors. Embodiments of this device can also be used as a preliminary diagnostic device when programmed to screen for selected or multiple diseases. The invention disclosed herein improves both the screening experience and medical outcomes. Those shown to be free of the VOCs constituting the disease or bio-threat "signature" can be allowed access to facilities with no immediate threat of spreading the disease. When a disease or bio-threat is indicated, the individual (and appropriate authorities) can be notified so that proper protocols such as medical referral or quarantine can be addressed. A "signature" in this context, is a composite of VOCs identified as being produced by cells of individuals infected by an identified microorganism or associated with a bio-threat. In addition, when used in a medical environment, through early detection and real-time test results, this invention can increase both survivability and quality of life of patients.

BACKGROUND

In the context of a viral disease, viruses require entry into cells for replication, infection and contagion. Viruses bind to specific receptors on cells and once the viral genetic material is incorporated into a recipient cell's metabolism, the virus hijacks the cells metabolism to perform virally related chemical reactions. These reactions are not normal healthy reactions of the recipient cell but reactions that have been introduced (e.g., from the viral genome) or accelerated, reduced or eliminated in response to the viral hijacking. In many viral attacks, an infected cell may recognize that it, the infected cell, is a hazard to its parent organism and will send signals to the parent to request an immune response. Thus, a collection of VOCs, some that may merely be indicative that a viral attack is occurring, while others will be a result of novel synthesis of viral components will manifest. Accordingly, a "signature" of a disease will not generally rely on a single VOC, but will consider a balance or ratios between several distinct VOCs. The VOCs of interest will generally be associated with the virus itself, but often will include specific information, e.g., of the infected recipient cell, that is cells of a type having a receptor that the spreading virus binds to before entering the cell. Understanding that the different viruses and different cells under attack will produce their respective signature VOCs, the device of the present invention can be programmed and/or designed to signal an alert for a single infectious disease of interest or to report results relating to a plurality of diseases or conditions.

The present invention has two fundamental components: the first for collecting, measuring and assaying VOCs in its vicinity, and the second for processing the VOC data into useful output with comparative analysis. This compact device is capable of rapidly assaying a non-invasively obtained bio-sample, and analyzing the relevant assay data for comparison against a designated library of signature data outputs to determine a particular subject's disease status.

The device assays for specific VOCs to identify one or more designated signatures associated with a particular disease or bio-threat. A distinguishing feature of this invention is its ability to rapidly obtain and analyze VOC data real-time from the assay of vapor components, rather than from solids or liquids. The device features durable sensor elements appropriate for mounting within a supporting structure, easily fabricated for durability and rugged use. The assay process using this device requires no chemistry, reagents, sample preparation or inter-sample maintenance. Only a cursory cleaning or wiping of the sensor rod may be advised before screening the next person or passing to the next operator.

An advantageous site for collecting VOCs is a warm site (for more robust volatilization) and a site with thin skin near active blood vessels. One such site is the axillary zone, aka, the armpit. The human armpit is known for its ability to produce sweat with its resultant odors or vapors. While weaker VOC signals may be obtained proximal to any body surface, the armpit area provides a higher concentration of VOCs thereby the time for collection and analysis while maintaining sensitivity.

FIG. 1 shows an analytical device 10 of the present invention with a detector unit 11, and an analytical unit 12. The detector unit 11 is physically aligned with a container 13 for presenting a liquid sample 2 into a sample zone 6. A physical alignment path 14, forms a pathway allowing Volatile Organic Compounds (VOCs) to traverse from the container 13 to the detector unit 11. The detector unit 11 includes a module 15 for delivering a vapor phase sample 1 to detection surfaces 16 that interact with the vapor phase sample 1. A detection surface 16 comprises a nano-sensor element layer 17 situated between an input 20 and an output 21. The input 20 is in contact with a base power source 22. The output 21 is in communication with a data collector 23. The nano-sensor element layer 17 is associated with a selection component 18 with specificity for a compound of interest 3. When the selection component 18 is in close proximity or in contact with a compound of interest 3, a signal 4 from the output 21 is altered. The signal 4 is collected by an analytical component 19 of the analytical device 10.

FIG. 2 shows an electronic module 30 that can be included in the analytical device 10. Module 30 analyzes and processes the output signal 4 to through an interface 31 produce a sample profile 32 and feeds the sample profile 32 through an interface 33 that compares the sample profile 32 with a signature 34 in a signature library 35. The interface 31 is shown with a receiving module 36 that produces a report 37 of signatures 34 that match the sample profile 32.

FIG. 3 shows a gas selective permeable membrane 5 that isolates the vapor phase sample 1 over the detection surfaces 16.

Figure 1:
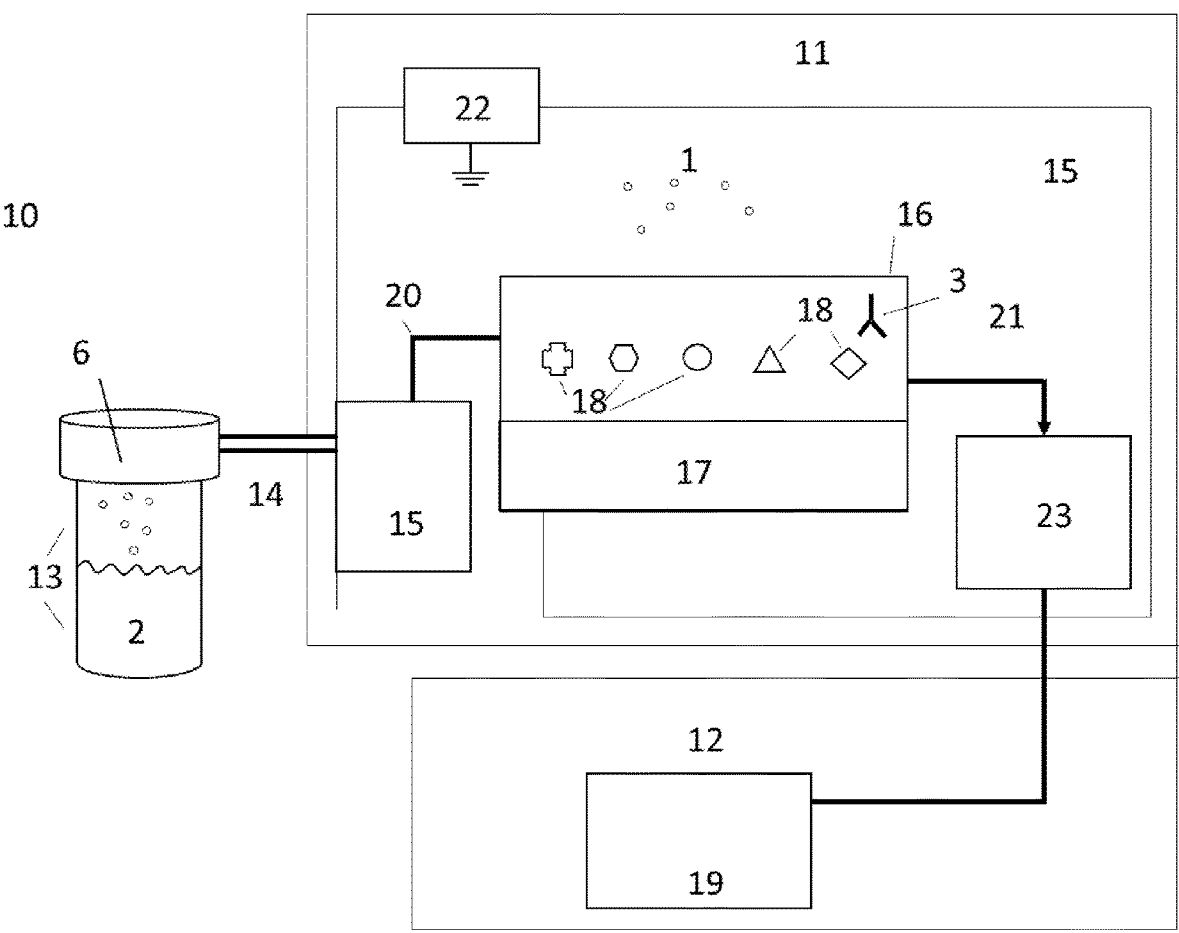
Figure 2:
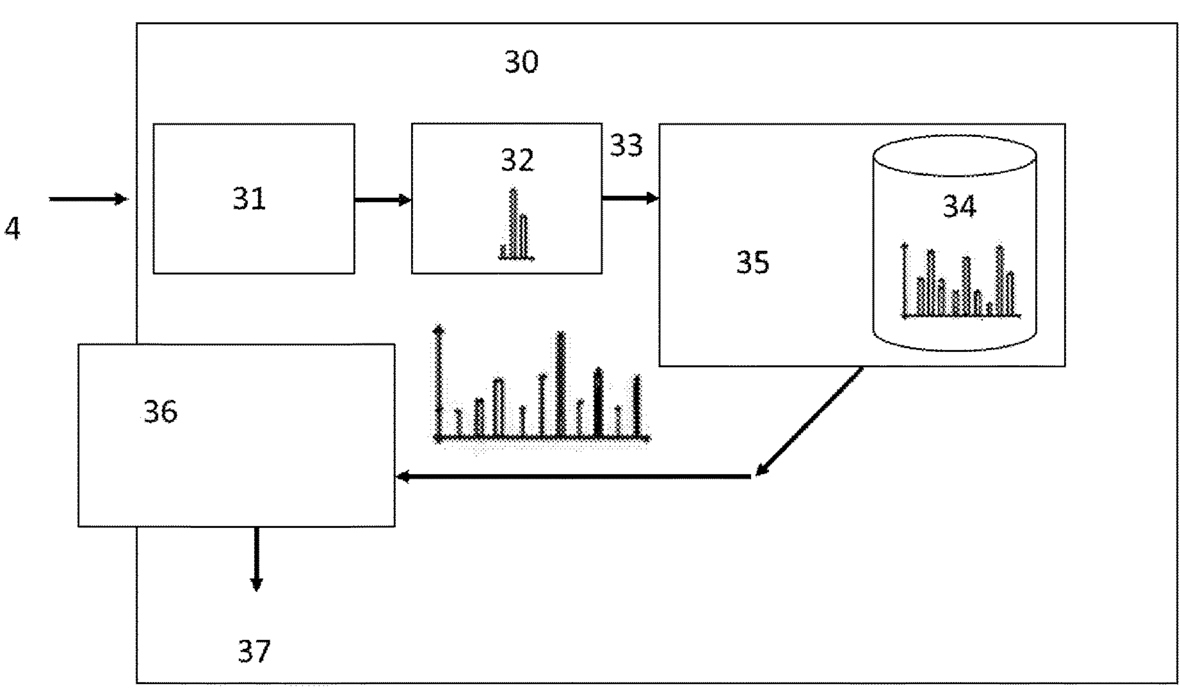
Figure 3:
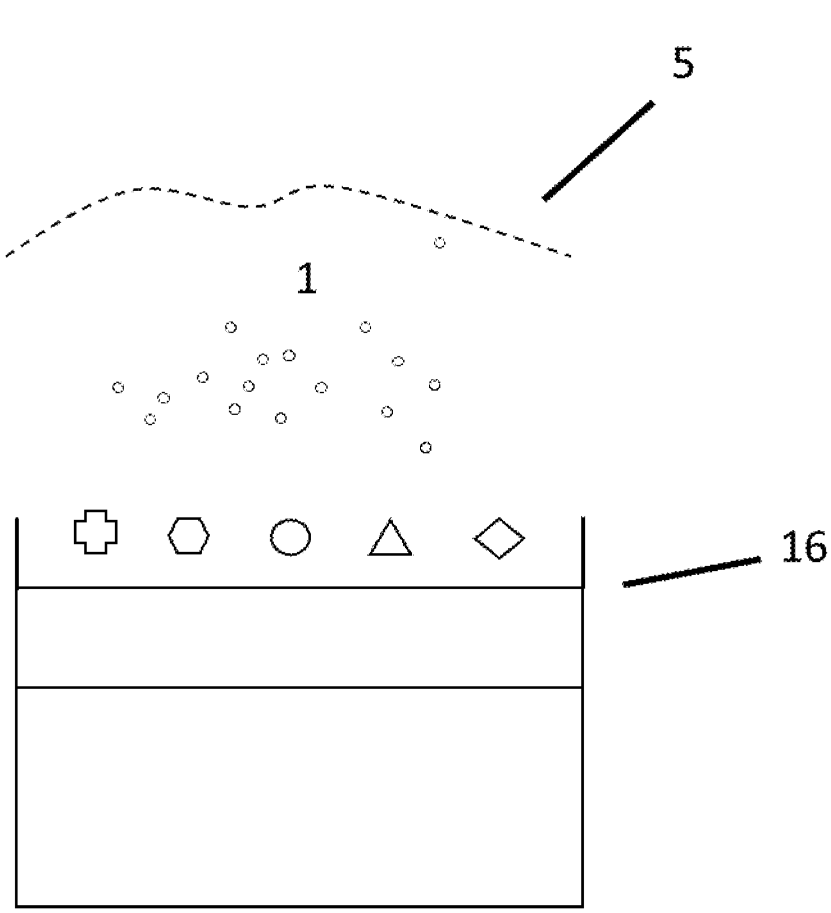
Figure 4:
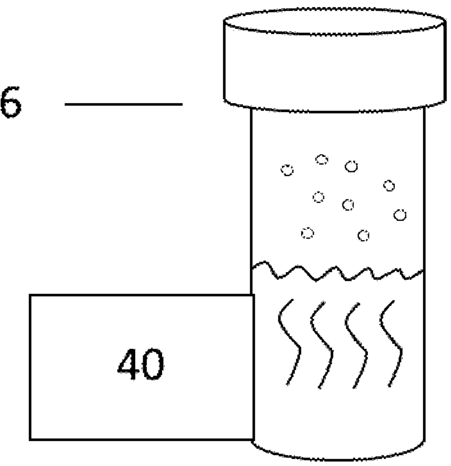
FIG. 4 shows a heat source 40 that can warm the sample zone 6.
Figure 5:
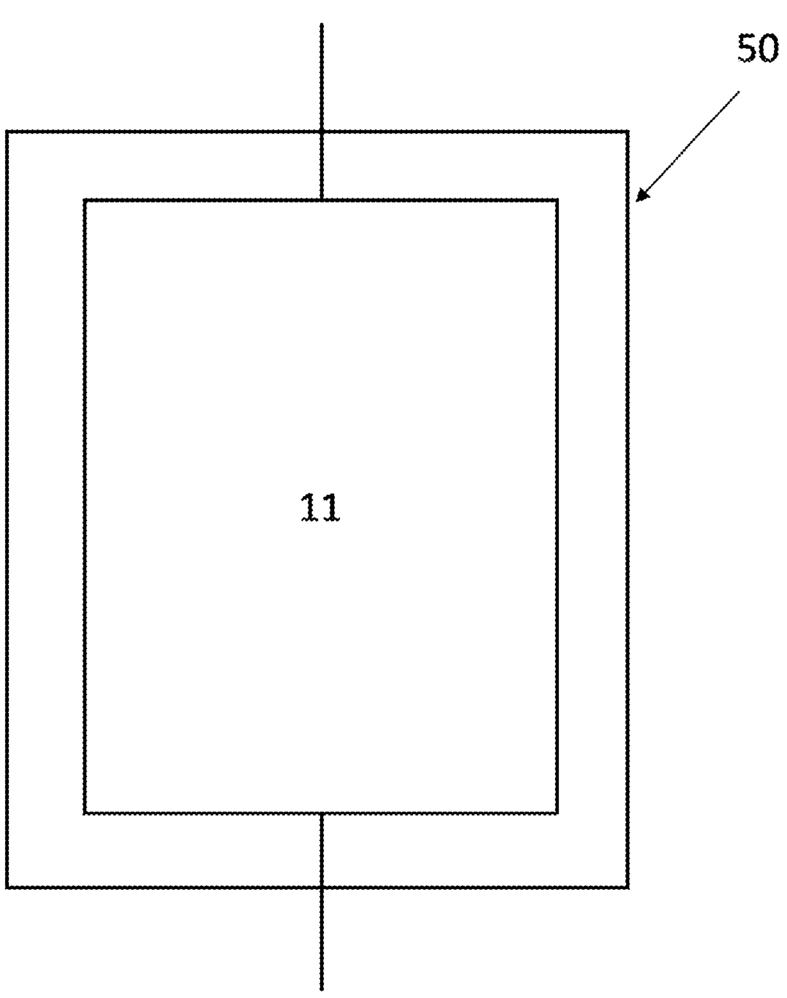
FIG. 5 shows a physical shield 50 that shields the detector unit from undesired physical effects.
Figure 6:
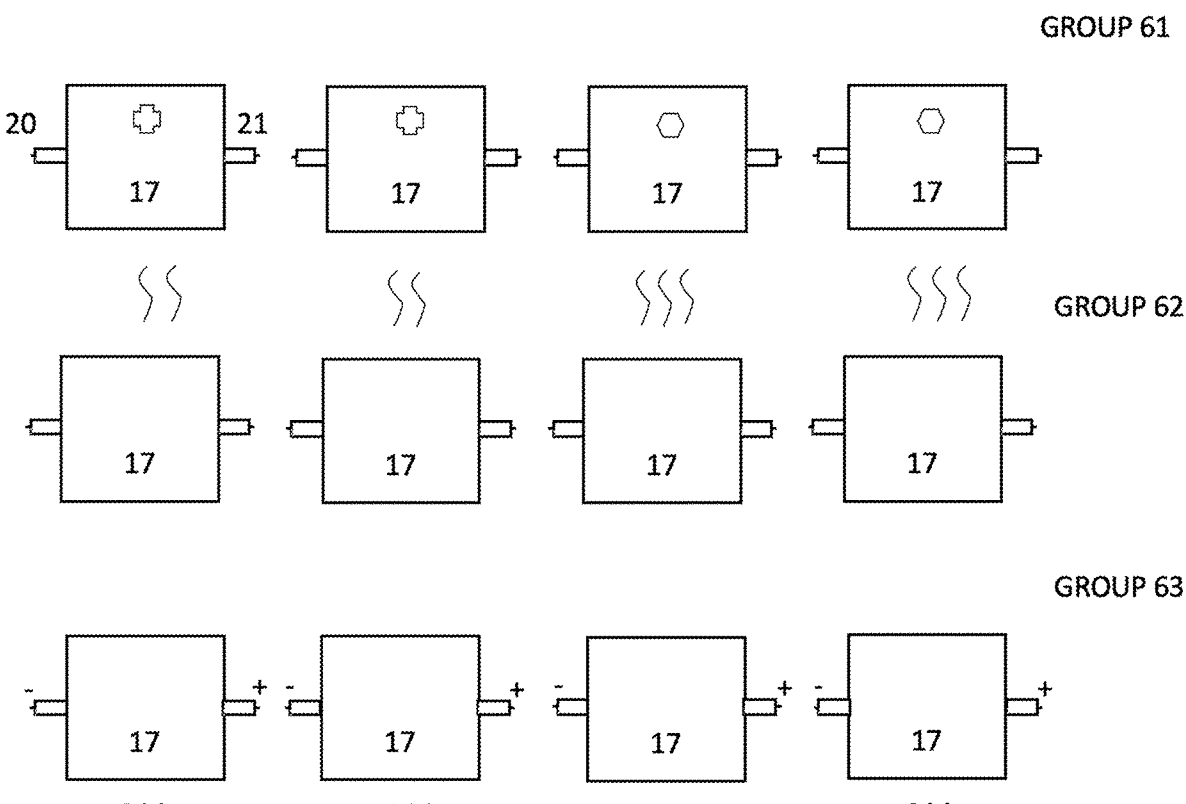

FIG. 6 shows an array of nano-sensor element layers 17 in groups 61 (distinct decoration 7), 62 (distinct temperature), and 63 (distinct base voltage) with distinct or different decorations 7.

DETAILED DESCRIPTION

At its simplest form, the device of this invention is a form of a scope, that instead of using electromagnetic signal particles (light) to form e.g., a microscopic or telescopic image to view as the information, forms a "signature" analogous to a multi-dimensional mathematical picture. This device can be considered analogous to an endoscope in that it non-disruptively views (by chemical analysis) what is provided by a pseudo cavity, an armpit. The endoscope, as known in the art, is used generally to sense light reflecting from the interior of a hollow organ or cavity of the body, for example, the esophagus. Instead of a physical shape as seen using an endoscope the device of the present invention views a "chemical" or chemo-behavioral shape.

The device may rely on natural convention and/or diffusion but speed and volume of collection can be improved when the "scope" (wand shaped probe-intercalated in the armpit pseudo-cavity) draws in air so that higher volumes interface with the nano-sensing element (NSE) that provides an electrical signal varying with its interactions with one ore more proximate VOCs. The moving air also can free or dislodge VOCs loosely adhered to skin or clothing. A gas selective membrane or filter allows vapors to cross into the analysis collection chamber while preventing interference from, e.g., dust or water droplets. Physical barriers or shields may be used in front and/or behind the armpit to reduce dilution from the surrounding air. A less simplified device may feature a warming or heating function that may stimulate release of sweat and VOCs and help to speed molecular arrival at the sensors.

Nano sensor pods arrayed beyond the membrane or filter are programmable charged to selectively attract or repel the panoply of VOC molecular species. The charge may be static on each NSE or may be varied to include consideration of charge effect on the molecule. An interacting and thus detected molecule will change the electrical characteristics of the NSE, transiently if only briefly interacting or longer if the affinity is greater. Changed charged and resultant disengagement of this molecule is one form of useful information that can be incorporated into the signature which may consider multiple scores of such events on different NSEs. The different NSEs may differ on charge provided, may differ on the decorations (functionalizing addends, e.g., short nucleic acids—e.g., 8, 9, 10, 11, 12, 13, 14, 15, 16, 17, 18, etc., natural or synthetic bases), may be maintained at different temperatures, etc.

Data from the NSEs may be analyzed and compiled within the device further analysis and report generation may be contemporaneous or batched processed following transmission (e.g., wirelessly or through a tethered cable) to an external computer or computers.

Thus, the assays obtained using device(s) of this invention initiate with a staff or baton guided to position a collection zone or chamber in the axillary area. A cap or shield structure at or near the terminus of the measuring staff may facilitate appropriate placement and act as a shield or barrier to airflow from outside the armpit. A second shield may be positioned at the back of the axilla, both to shield the armpit from the outside air during data collection and to shield the test subject from others, e.g. the device operator. Gases are collected passively or actively within the scope and allowed to pass in close proximity to at least one array of nano-sensor elements NSEs. The NSE responses are monitored and recorded for analysis of responses from the various NSEs. The analysis and/or subsequent analyses produces signature data for comparative use in identifying subjects infected by an organism under investigation or a possible unknown bio-threat.

The device may report results by a simple signal, e.g., a tone, a light, a locking of doors, etc. The signal format is not restricted, perhaps a tone or light frequency may divulge important information; e.g., a high beeping tone or flashing red light may signal that the subject should not be allowed to proceed; a soothing tone or green light might indicate passage is approved, etc. More complex signals such as voice commands, lights progressing down a desired path, arrows or physical prodding or gate opening are also potential signals.

A more elegant probe device may feature an umbrellalike structure that may be retracted when passing through or under the axilla, then opened as the device is pulled back to provide the front shielding functions. The length of the device may be telescopically adjusted to allow selective control of the distance between operator and subject.

After VOC data collection and analysis, the signature information is available to the operator and/or subject and is preferable compiled and further analyzed across multiple subjects to continuously improve or fine tune the devices. The volumes of data obtained suggest that machine learning or artificial intelligence will be involved.

The present invention features a rod or baton having a cross section which be circular, elliptic, oval or otherwise, extending from a handle or trigger mechanism. The (cylindrical) rod portion incorporating the sensing module is designed to be placed within a subject's armpit area for collecting body odors (VOCs). The collection and measurement portion of the rod is surrounded or enclosed by a perforated sheath that maintains a form factor with headspace between the device and skin or clothing and into which VOCs and other bodily gases will enter. A heating element may be used to increase or aid in the volatilization and diffusion of gases by gently warming the surrounding tissue or clothing. In many embodiments a vacuum system will draw vapors emanating from the body into the device for analysis.

In certain configurations, the rod or baton may have a plate-like structure opposite the handle. This plate-like structure can be used to achieve optimal placement of the device on the subject for assay and help to isolate body VOCs from the environmental air. This end plate will be large enough to prevent the device from sliding backwards out of the axilla when the arm is rested against the chest area, but not so large in dimension to prevent the endplate from contacting both the arm and torso. A disk about 5 cm or larger in diameter is suitable for most persons. The disk need not be circular and may have an area or receptacle for attaching a padding and/or a disposable contact shield. The endplate may be swivelly attached so that it does not necessarily form a right angle with the baton. The endplate may be set off center from the baton, e.g., having a larger surface area above rather than below the wand. A second plate may be more proximal to the handle. Such second plate may be useful for isolating a sampling area along the wand between the two plates. In some embodiments, the second plate may be larger than the end plate, e.g., to provide a substantial physical barrier between the operator and the person being screened. The second plate may be off-center, e.g., to better shield the facial areas of operator and subject from one another, for example, extending to the subject's spine or farther. A barrier extending towards the midline ~25 cm or more is one example. Such barrier may be transparent. In embodiments where, for example, a two-meter or six-foot social distancing protocol is the norm, the wand, if handheld by the operator will be or be extendible to be in compliance.

Sweat is an available source for sampling as the apocrine and eccrine glands filter body fluids and secrete water for cooling and odors for recognition and other legacies. Thus, information from the entire body is available in sweat.

In some embodiments, e.g., when shielding is not deemed necessary, the plates may be frame-like, spiraling, spoked, carrying a logo, etc. Plates may be color or otherwise coded to indicate, e.g., the disease being screened, an acceptable specificity and/or sensitivity, a design for man, woman, child, etc.

In one exemplary use, a person being screened (the subject) steps on a marked spot on the floor. The subject is advised to raise one or both arms. The wand is inserted in the axillary area and the subject is asked to lower the arm(s). The wand is retracted so that the endplate comfortable contacts the arm, shoulder, and/or torso of the subject. The second plate then slides to contact the subject's back helping to isolate the test area and the subject remains in place until instructed to raise the arm(s).

For rapid screening a subject may be advised of a positive result at this stage and advised to seek treatment. Optionally the second axilla may be similarly assayed for confirmation or to suggest further screening. Since in many instances the screening device will only contact clothing, not the subject, strict cleaning protocols may not be advised. For subjects whose clothing exposes the armpit area a sleeve over the wand may be advised. In several embodiments the wand is surrounded by a perforated or porous, e.g., open foam padding which can be designed to be washable or disposable.

The present invention especially features a collection module wand or tube-like structure that is placed in contact with the armpit or axillary area. Signatures are not limited to any single VOC, class of VOCs, select groupings of VOCs, amalgamations of cross reacting VOCs, etc. and may be analyzed in one or more algorithms involving non-VOC and/or alternatively sensed or obtained data. Such data may include but is not limited to genetic data, age, gender, health history, ambient or internal presence or concentration (e.g., from circulation, tissue sample, ambient gas, temperature, season, blood work, stool work, urine sample, skin sample, hair sample, other bio-sample (e.g., saliva, spit, tear mucus, time of day, light level, travel history, etc.). Examples of VOCs and or other relevant compounds that are available for analysis include, but are not limited to: androstenol, dehydroepiandrosterone, dehydroepiandrosterone sulfate, androsterone, andosterone sulfate, lactic acid, acetic acid, isovoleric acid, cholesterol, 5-androst-16-en-3-ol, aniline, o-toluidine dodecanol, progesterone, one or several ketones, one or more fatty acids, one or more fatty esters, one or more alcohols, ethanol, hormones, steroids, endogenous cannabinoids, styrene, naphthalene, benzaldehyde, tetrachloroethylene, propanol, diphenylamine, butanol, pentanol, $H_2S$, $CH_3SH$, $(CH_3)_2$, dodecanol, tetradecanol, 2-ethylhexanol, phenol, p-cresol, 2-methylaniline, pyridine, 3-hydroxy-2-butanone, propionic acid, iso- and n-butyric acids, phenylacetaldehyde, furfuryl alcohol, isovaleric acid, α-methylbutyric acid, dimethylsulfone, n-dodecanol, n-hexadecanol, p-cresol, indole, benzaldehyde, benzoic acid, ethylene glycol, propylene glycol, propanoic acid, n-butyric acid, hydroxy-ketones, isobutyric acid, 3-hydroxy-2-butanone, 2-methylbutyric acid, 2-hydroxypropanone, valeric acid, myristic acid, palmitic acid, phenylacetaldehyde, palmitoleic acid, steric acid, oleic acid and urea.

As an analogous example, compounds that have been measured in breath and/or surrounding ambience include, but are not limited to: butane, 3-methyl tridecane, 7-methyl tridecane, 4-methyl octane, 3-methyl hexane, heptane, 2-methyl hexane, pentane, 5-methyl decane, IL-6, endothelin-1, methylated-including monomethylated—and other branched alkanes, acetaldehyde, formaldehyde, 2-methylpropanal, 3-methylbutanal, 2-methylbutanal, butyl acetate, 3-heptanone, 2-amino-5-isopropyl-8-methyl-1-azulenecarbonitrile, 6-ethyl-3-octyl ester-2-trifluoromethylbenzoic acid, 2,3,4,6-tetramethoxystyrene, 2,4,6-tris(1-methylethyl)-phenol, 1,3,5-cycloheptatriene, and 2-methoxy-acetate ethanol, butylated hydroxytoluene, 1-methyl-3-(1-methylethyl)-benzene, and 4,6-di(1,1-dimethylethyl)-2-methyl-phenol, 2-amino-5-isopropyl-8-methyl-1-azulenecarbonitrile, 2,2-dimethyl-decane, carbonic dihydrazide, 4,6-di(1,1-dimethylethyl)-2-methyl-phenol, butylated hydroxytoluene, 3,3-dimethyl-pentane, 5-(2-methylpropyl)-nonane, 2,3,4-trimethyl-decane, 2,2,4,4,6,8,8-heptamethyl-nonane, ethyl benzene, 2,2,4,4,5,5,7,7-octamethyloctane, hydroxymethyl 2-hydroxy-2-methylpropionate, 2-methyl-hexane, etc.

A graphical representation of the VOCs may be displayed, stored and/or printed if desired.

A chemical breakdown of the VOCs may be made available in a report, for example a detailed report that includes intensity of each relevant component. Historical data may be stored and compared with to determine if a particular course of treatment has been effective in reducing the signature VOCs. Similarly, for prolonged care, the progression of, for example, a cancerous disease or autoimmune syndrome may be plotted and followed using the acquired data.

Advanced Analytics

To date laborious techniques such as MS/GC have been the preferred analytical tool for VOC analysis. Improvements in detection sensitivity from micro-detection to nano-detection using highly advanced sensors now enables a more robust use of nano-analysis of VOCs and other compounds and when combined with rapid data analysis and machine learning can: a) confirm a diagnosis, b) assist in selecting or ranking diagnoses and/or c) suggest one or more diagnoses even prior to outward symptoms becoming apparent. After assay, in some circumstances simply questioning a patient about a result may elucidate an overlooked symptom of disease.

The general approach of monitoring VOCs for detecting disease has been in development for several decades and now is soundly acknowledged in developing science and health medicine. In accord with the present invention a device to achieve these VOC assay goals has been designed to assay a variety of volatile organic compounds (VOCs) in a rapid and reproducible fashion. Under the present invention, multiple disease signatures can now be searched from the same sample simultaneously. The basic benefits of measuring VOCs for disease detection have been recognized in medicine for quite some time. In a 2014 Clinical Policy Bulletin, Aetna explained its policy regarding VOC analysis at that time as:

Aetna considers the analysis of volatile organic compounds experimental and investigational for the following indications (not an all-inclusive list) because the clinical effectiveness of this technique has not been established:

- Detection of bacteriuria
- Detection of cancer (e.g., breast cancer, colorectal cancer, lung cancer and cancer of the pleura, pancreatic cancer; not an all-inclusive list)
- Diagnosis of amyotrophic lateral sclerosis
- Diagnosis of autism spectrum disorders
- Diagnosis of inflammatory bowel disease
- Diagnosis of juvenile idiopathic arthritis
- Diagnosis of non-alcoholic fatty liver disease
- Differential diagnosis of breast diseases (e.g., breast cancer, cyclomastopathy, and mammary gland fibroma)
- Prediction of development of childhood obesity
- Use as markers for monitoring hemodialysis efficiency[1]

[1] Clinical Policy Bulletin: Analysis of Volatile Organic Compounds. Number: 0717. Revised April 2014. Obtained from: http://www.aetna-.com/cpb/medical/data/700_799/0717_draft.html Advances in VOC Technology Urine, exhaled breath and blood are recognized as available sample sources. The present invention features axillary vapors, e.g., sweat by-product, as a primary source for the assay.

A device, as described herein, capable of providing signature information from a variety of assays, including bioassays or assays of structures suspected of emitting possible harmful compounds into ambient atmosphere meets multiple identified needs and applications.

The device of the present invention provides rapid highly sensitive detection of VOCs in a gas phase sample, e.g., vapors collected by the device held in the armpit. Analytical data are then processed using the device's library of algorithms to detect a disease or to answer questions for which the sample was taken. Through machine learning and artificial intelligence, the device is continually developing and improving its algorithms.

Through capturing the VOCs in vapor or gas phase to measure the presence, amounts, volume, intensity or strength of signal of multiple VOCs, then classifying each signal as from the organism or the environment and removing foreign VOCs from analysis consideration, the device then outputs a sample's gross output of organism initiated organic compounds for comparison to the signature database to determine whether a specific disease (or set of diseases) is present. The present invention continues to consolidate VOC signature profiles into a library as new sample outputs are presented.

In an example where a specific condition or disease is targeted for identification, the system may be trained using VOC readings from an identified afflicted cohort compared against readings from a non-afflicted cohort. Machine learning identifies features, e.g., presence or absence of behaviorally defined VOCs, ratios between VOCs, level of one or more VOC, etc. "Behaviorally defined" is a term chosen to emphasize that the device and system operate without a requirement to chemically characterize (identify) the VOCs involved in analysis. Movement or retention of a molecule in proximity to an NSE in a receptor array provides the criteria for recognizing the VOC through artificial intelligence (AI) analysis. The learning data from the compared groups is then tested in at least a second set of afflicted/non-afflicted individuals for confirmation or refinement of detection criteria and to establish specificity and sensitivity. Subsequent analyses continue to improve these values.

Where identical or similar types of NSEs are present in an array, the related NSEs may be considered as alternatives in a group for AI analysis. An individual device may self calibrate using a standard VOC set to weight each NSE within a cohort depending on its calibrated response. For example, an NSE may be assigned a multiplier that modifies the time of interaction with a VOC, a threshold value may be assigned, a strong or weak signal from a single or subgroup of similar NSEs may dominate or override signals from others. Arrays may be configured in a cartridge format allowing rapid replacement or exchange. The exchange factory may provide a replacement cartridge reprocess and reboot the one received.

If the device senses contamination or degradation of signal output, reaches an expiration date, or approaches a predetermined number of assessments, the unit in a preferred embodiment, signals the operator or maintenance provider to replace its sensor cartridge. Such cartridge can be ejected using a simple release mechanism, as is common in the art, before replacement by merely sliding or snapping in the new one. When the device is optimized for detecting a specific disease or disease class, the specific disease can be easily changed by exchanging the cartridge for another with different specificity or in some instances adjusting the test pod or array, e.g., by altering software, temperature, base voltage, etc., While one or a plurality of known diseases or conditions are being addressed in VOC assessments the system has the capacity to recognize additional disease or conditions not specifically addressed in a signature in the library of disease signatures. The system can identify groups of analyses that share common traits that are not previously recognized but that are widely shared across a restricted sub-population. For a novel disease with a consistent presentation pattern may be recognized in a sub-population numbering only a score or fewer. Post hoc analysis using medical records anonymously associated with the VOC analyzed individuals may expand the pool of disease/condition signatures for system identification. Continuous assessment of commonality identified sub-populations or groups can expand the repertoire of diseases/conditions signatures in the system. It is to be expected that widespread use of the device may identify a group to be investigated as potential early carriers or sufferers from a novel disease. For example, a set of individual profiles may present with commonalities not associated in any recorded signature. Such profiles may contribute to a signature for an as yet to be named disease.

The present device can participate in a system of devices, e.g., similar sensing devices used in clinics, used for access control to venues, screening devices used at ports of entry, screening international travelers, etc. These devices, can share their data pools with others devices using VOC sensing arrays to build and maintain growing signature libraries covering multiple diseases and conditions. The sharing may involve controlled, e.g., licensed downloads and/or uploads to maintain legitimacy, privacy concerns, consistency, etc.

An optimization step may augment signature identification and development. In one such optimization protocol VOCs are assigned to two levels. A strongly interacting VOC level A and a weakly interacting level B. One or more B level VOCs are chemically analyzed to determine atomic content and molecular structure. Conventional analyses including, but not limited to GC-MS, X-ray diffraction, Inductively Coupled Plasma Optical Emission Spectroscopy, etc., identify the compound(s) of interest. In tautomerizing compounds one may be favored to continue the optimization protocol. Once identified and selected, the compounds are analyzed for interactions with NSE decorations. Potential new decorations are tested for stronger or more specific interactions with the NSE. NSEs are decorated with the novel potential decoration candidates for improved interaction signaling. When a tautomeric compound is of interest, decorations may be selected for more specific or robust interaction with one of the tautomers. Such interaction may favor or "freeze" one of the tautomeric forms as a facet of interactions between the NSE and compound. Following this or a similar protocol a sensor array may be optimized for a specific disease or condition or one or more of the similarly decorated NSE groups may be substituted with the decorated NSE sporting improved discrimination towards optimization for a selected disease, class of, condition, etc.

In addition, the device may physically incorporate add-on devices and/or applications, for example, a capillary analytical attachment, including, but not limited to: capillary electrophoresis, capillary chromatography, capillary ELISA, nano-sensors similar to the vapor phase sensors but proximal to analyte in a liquid phase, etc. Add-on devices may be analytical providing additional information to be used in data analysis and signature identification or in some embodiments may absorb, adsorb, catalytically modify and/or filter out potential confounding compounds and thereby minimize the necessity for applying algorithms to remove the undesired ambient VOCs. The machine learning component of the invention, in preferred embodiments, has capacity for inclusion of externally generated information from add-on devices and/or from externally provided information.

One preferred format of the present invention features "chips" with modular nano-sensing (or nano-sensor) elements element) that are independently maintained at a fixed, fluctuating, stochastic, alternating, discontinuous or flashing feeder power supply. The outputs of each NSE may be individually wired to a dedicated data transducer or a selection of sensor outputs may use a common carrier circuit and thus be "averaged". In some embodiments, a simpler circuitry may involve multiple elements feeding a single output that may sum the outputs to deliver an average reading. When one or more of the "averaged" sensors is turned off or powered down, the average will not include output from these one or more powered down sensors. When input sensors are powered individually, for example, in a cycling pattern when only one (or a selected portion) of the input electrodes being charged, averaged outputs synchronized with the timing of input charging can thus provide data from individual channels.

Sensors may act independently and/or in concert: in parallel or in series. During development, signatures may be derived from multiple sites including, but not limited to: ambient environment, body secretion (internal or external), natural orifice, artificial orifice, etc.

The single output may connect and thereby collect data signal from any desired fraction of elements. For example, a single output may receive signal from all elements on a chip, half the elements on a chip, one-third the elements on a chip, a quarter the elements on a chip, a fifth the elements on a chip, and so on, for example, $1/6$, $1/7$, $1/8$/, $1/9$, $1/10$, $1/12$, $1/20$, $1/25$, $1/33$, $1/50$, $1/100$, etc. Any output may be associated with 1, 2, 3, 4, 5, 6, 7, 8, 9, 10, 11, 12, 13, 14, 15, 16, 17, 18, 19, 20, 21, 22, . . . , 24, . . . , 32, . . . , 48, . . . , 50, . . . , 64, . . . , 96, . . . , 100, . . . , 128, . . . , 200, . . . , 250, . . . , 256, . . . , 500, . . . , 512, . . . , 1000, . . . , 1024, . . . , 2048, . . . , 4096, . . . , 5000, . . . , 8192, . . . , 10,000 ($10^4$), . . . , $2^{15}$, . . . $2^{16}$, . . . , $10^5$, . . . , $2^{17}$, . . . $2^{18}$, . . . , $2^{19}$, $10^6$, . . . , $2^{20}$, . . . , . . . , etc., total number of sensors on a chip which may vary with time or programmed instructions. The precise count of sensor elements associated with any output in general is a design feature and does not define operative functions of the invention. The counts specifically exemplified above are exemplary low numbers of sensors that may feed an output and higher numbers common in conventional plate assays and powers of 2 and 10 frequently used or approximated in biological or chemical science or physics or electronics.

When connected to multiple elements, the output averaging output signals from each, connection of each element is optionally modulated to alter weightings of elements in the average. With fluctuating or non-constant inputs weighting is also controllable. For example, in an extreme sense a stochastic or alternating input, when alternated to off that element's output will report a zero weighting, or a fluctuating or stochastic feed can serve to physically, rather than mathematically control the weighting output. The designer and/or operator will have options for mathematical/algorithmic or physical/electrical weighting of each NSE input to the data analysis. A group of elements may therefore receive the same feeder voltage, or the feeders may be independently controlled.

Instruction to or control of the system may be through information encoded on a sample package, information encoded on a sensor chip, from a user interface, information provided remotely by machine or active user, or information encoded within the device. For example, samples may be encoded with a shape or mass signal. A sample having a given shape would instruct the device to proceed with the assay that the software associates with that shape. In addition to shape, sample cartridge mass may be instructive as to the sample mass itself or may, perhaps distinguishing a smaller or a larger sample, instruct processing of the sample to allow access at controlled volume or feed rate of the VOCs into analysis. An optically readable signal, (color, transparency, bar code, text, etc.) an electronically accessible signal (RFID, memory chip, or drive, etc.), a magnetic signal, etc., are also usable in controlling the device. Specific control can be through a large variety of means and is not generally to be considered as limiting the invention. The signal embedded itself may be adequate to program the relevant machine cycles or may instruct the machine to access further instructions for example, in machine archives or at a remote location. A device may cycle through one or a plurality of signals as directed or required. Chips may be interchangeable and be encoded using signals analogous to those discussed above relating to sample cartridges.

When the sensing rod is positioned for assay, the operator may manually initiate the collection process. The operator may visually and/or tactilely determine that the sensing device is in position; may ask the subject if the device is comfortably situated within the armpit; a predetermined time has elapsed following placement in the axilla; and/or receive feedback from the device to indicate that conditions are proper for the assay to proceed. The device may inform the operator of proper conditions by any suitable means, e.g., light, sound, movement of a switch or switch guard to a ready position. A vibration or similar tactile signal may be especially useful in crowded, noisy venues. In some embodiments, after positioning of the device in the armpit, initiation may be triggered temporally, mechanically or automatically, e.g., using light, tactile sensors, and/or temperature sensors.

The collection process may include a heating stage as a prelude to actual driving the armpit gases through to the sensing zone or chamber. In a simple understanding the flow of gases, including VOC gases moves across the sensor elements from a higher pressure to a lower pressure zone. The lower pressure to invoke net diffusion of gas may be made by forming a slight vacuum in the sensing module distal from the exterior (where the armpit is). A blast or flushing gas is another option for creating or enhancing the pressure difference. The blast or flush can stimulate or liberate loosely bound VOCs from their resting sites and thereby facilitate collection. A portion of the device may be exhausting a volume of gas that will serve to transport VOCs to the sensors. The flow may essentially be constant or stable. It may be from the exterior across the NSEs to an exit. Flow distal to the NSEs may assist in collecting or driving gases to the NSE zone.

Though the flow is essentially constant, the flow rates over the NSEs or driving VOCs towards the NSEs may be pulsed, i.e., varying in regular (e.g., continuous waveform similar to a sine wave, spikes, etc.) or irregular (e.g., asymmetric, perhaps a ramp or wave upstroke with a different shape downstroke including a vertical drop). The pulsing continuing flow may feature a flash start of a strong pulsed flow with a ramped or declining wave to continue flow but preparing for the next pulse. In some embodiments the pulsing waveform will directionally pulse the vapors (VOCs also) towards a sensing chamber that may analyze the bulk or fractionate a portion for alternative analysis.

Some embodiments may feature a chamber that captures a volume of the ambient armpit gases and then delivers all or at least a portion of the chambered gases to the NSEs. The gases that have crossed sensor elements will differ from those entering as the NSEs retain respective VOCs during analysis. These may be restored to the exhausted sample(s) using a flush of clean or inert gas coupled with decreasing the interactions between sensors and VOC molecules by localized heating and/or changing the electric charge. A portion retained may be delivered to the NSEs, e.g., following changing the temperature of the captured gas, allowing the vapors to react for a designated time, photo-reacting the captured VOCs before delivery to the NSEs, etc. In specialized cases, the retained chamber gases may be made available to another assay device or a different set of sensor elements.

During sensing, a meter (visual, sonic, photonic, etc.) may be actuated to indicate progress. For example an analogue styled meter may have colored zones in a bar or pie shape format to light when the subject's armpit is engaged with colored zones or separate bars to indicate time of or time to completion of one or more stages, e.g., a heating stage, a collection stage, an analysis stage, etc. Rather than time, the display may indicate temperature, volume or a count of VOC molecules crossing the sensor pads. Sound or light cues can be provided at various evens in the assay. For example, a blue light may indicate the rod is properly situated and ready to begin. The "begin" may relate to initiation of the collection-analysis process that in some embodiments includes a warming phase. The color may change as different phases are actuated, e.g., a color for ready, a color for warming, a color for collecting, a color for completion. At completion different colors can indicate different outcomes. For example, green to indicate the subject is not a risk; red to indicate a risk of contagion.

A remote location providing instruction, collection, processing, and/or storage of data may be proximal to the device, i.e., in the same building, or may be distant, e.g., an unknown location in the cloud. Instructions may be self-sufficient or may query for further input from an operator or a distant database. Remote instructions may be signaled for production and delivery, for example, when the device is actuated by turning on or introducing a sample. Instructions may be stored in an arbitrary location such as the cloud which the device queries for specific operational signals. Remote signaling may be updated in accordance with experience of sister devices which can involve a neuro-like network. The remote instructions may be of any form, for example, explicit temporal instructions relating to each controllable variable, or more simply, to instruct to initiate one or a series of protocol apps available to the machine. For security purposes the device may require identification such as an access card, access code, facial or bio-recognition, etc. to shield against unauthorized use. The device may be configured in many formats, e.g., as a portable point of care device, a mobile high throughput application, a fixed regional installation for massive scalable testing, etc.

Organization of NSEs

The sensor elements are preferably nano-sensor or nano-sensing elements (NSEs) to minimize size and maximize sensitivity of the sensing chip. NSEs will in general be mounted or carried on a substrate or support matrix forming a "chip". Individual matrices may feature multiple elements, generally 10 or more, 32 or more, 50 or more, or larger populations of elements on a single chip. As a rule, a greater number on a chip promotes a compactness desired for minimizing weight and size. The number of NSEs is a design feature and can mimic numbers familiar to the operator or data analyst. For example, multiple of the number of wells common on petri dishes may facilitate using existing software tools to further analyze and compare results. Powers of ten, multiples of a hundred or thousand, powers of two are in common use. Accordingly, about 96 elements, 100 elements, 128 elements, 144 elements, 200 or 256 elements, 500 or 512 elements, $10^3$ or $2^{10}$ elements, $10^4$, $2^{20}$, $10^6$, etc. may be built in as common useful working populations even if several elements on the chip are not activated.

Minor variances in sensor sensitivities may be weighted internally by the machine software or may be overcome by averaging signals of a sub=population of chips. This massaging feature is available as a tool to promote inter-device and/or inter-chip consistency.

NSEs carried on the chips can be any properly designed sensing surface which is capable of donating, receiving, or altering the flow of electrons, for example, field-effect transistor (FET) or other physico-electrical property/activity including, but not limited to: semi-conducting nano-wires, carbon nano-tubes—including single-wall carbon nano-tubes, chitosan-cantilever based, synthetic polymers—including dendrimers, plasmon resonance nano-sensors, Förster resonance energy transfer nano-sensors, vibrational phonon nano-sensors, optical emitting, optical frequency (or wavelength) based nano-sensors (sensitive to photon transmittance, absorption, reflection, energy modulation, etc.). Nano FETs and other nano-sensor formats generally operate by changing electrical properties as a substance comes in close proximity to the sensor by perturbing the steady state (absent the proximal substance) charges and movements (distribution of electrons) within the nano-sensor. When the transistor effective electrical properties cause an observable change in electron flow (current) this manifestation is one example of sensor competence. The altered distribution of electrons, depending on the design of the nano-sensor, changes one or more electrical properties, e.g., impedance, resistance-conductivity, capacitance, inductance, etc. and thus the physical movement of a detectable particle, e.g., an electron, a photon, etc.

The discussion in this disclosure of the present invention primarily features nano-sensors whose characteristics change depending on association (close proximity) with a chemical substance. Sensation may involve more than one event. For example, in one format of nano-sensor the proximity event may dampen a vibration that is sensed by observing a changed electrical property. Similarly, an optical property, e.g., reflectance, transmittance, refractive index, can be perturbed by proximity to a substance, altering electron distribution within the sensor enough to cause optically detectable geometric changes. The optically related detection format for a nano-sensor may be observed at a specific frequency or range of frequencies, for example moving peak transmittance to another frequency.

Nano-sensors are classified in different ways, for example, the feature being assayed, e.g., movement, temperature, frequency, chemical, current, voltage, etc.; or output, e.g., fluorescence, light, electric property, etc. For example, a fluorescence outputting nano-sensor may be carbon based, e.g., single walled carbon nanotube, graphene, quantum dot based, nucleic acid (RNA, DNA), peptide based, organic polymer based, etc. Photo-acoustic, plasmonic, magnetic, etc. perturbations are also useful as biosensors and may be applied in features of the present invention.

Embodiments of the invention may be designed for ambient temperatures and pressures common on earth, but special designs may be configured for vacuum or high pressure, zero or micro-gravity, extreme cold (including biologic storage freezers, liquid He, superconducting cold environments, furnace temperatures, combustion chamber temperatures, etc.

One format extensively described as an example herein involves use of carbon-based structures having properties similar to decorated single wall nanotubules (SWNTs). The carbon component atoms of the nano-tubules are receptive to complexing with ringed chemical structures (decorations or functionalizations), often occurring through a non-covalent It-bonding effect. Graphene, having similar single layer carbon geometry, with proper decoration, can also serve as a sensing surface. Evidence indicates the curved carbon structures of the SWNTs demonstrate more consistent FET properties in many use environments with various functionalization (decoration). Therefore, crumpled or curved graphene, possibly formed into a corrugated, or spiral geometry, (See, e.g., Michael Taeyoung Hwang, et al., Ultrasensitive detection of nucleic acids using deformed graphene channel field effect biosensors. *Nat Commun* 11, 1543 (2020). https://doi.org/10.1038/s41467-020-15330-9) may demonstrate more promising specificity, speed of analysis, and/or sensitivity over planar graphene for particular applications. As nanotechnology continues to progress additional sensor formats such as those emitting light, will become accepted in the art. Embodiments of the present invention may incorporate these improved sensors as their reliability is established. The skilled artisan will generally choose which form of sensor is optimal for performance and cost.

In addition to the field effect electrical sensing set forth as a preferred embodiment, other qualities of thin carbon based used for sensing are possible. Optical, electrochemical or electrical features have been employed with graphene-based biosensors. Forms of graphene have been successfully tested for electrochemical (amperometric, voltammetric, impedimetric, or combinations thereof) and electrical sensing applications. Selected formats have the high electron transfer rate, the high charge-carrier mobility and manageable electrical noise that is necessary for sensitive detection of biomarkers and other biological analytes. Successful assays have been reported in both serum and blood extracts. Optical transparency of graphene monolayers allows use in sensors such as optical-based G-biosensors.

The NSEs themselves or at least portions of the device surrounding the chips are preferably surrounded by a controlled gaseous atmosphere, generally slightly above ambient pressure when the gases are used to maintain inflation and shape of the sensing module. The sensing chamber itself may have a reduced pressure with respect to the sample introduction area helping to draw VOC gases into contact with the NSEs. A positive device pressure at at least one level surrounding the assay chamber is generally preferred to minimize possibility of contaminating inflows. The actual pressure where sensing is accomplished however can be varied. VOCs may be delivered by having a negative relative pressure in the chip area with respect to a sample containment or introduction area to cause drawing in sample off-gas when the off-gas collection volume and the sensing volume become connected. VOCs themselves, for example, when heated may produce the pressure difference to drive delivery to the sensor volume.

Since physical delivery or movement is required to bring a candidate compound in contact with an NSE, a physical intervention is often required. Physical movement can be induced as desired by any appropriate force. Forces may be constant, variable, stepped or pulsed, etc. Multiple forces may be used in series or parallel for sample delivery or a single force may be selected from the device's repertoire to enhance delivery and detection of the sample to the NSE(s).

For example, temperature can control speed and movement of target compounds and ambient gases driving the sample compounds to the sensor; pressure difference can induce a convective movement. Pressured gas canisters may provide the driving force. Other forces including, but not limited to: electric, magnetic, electromagnetic, acoustic, photo-excitation or photon momentum, etc., may be selected depending on particular circumstance. Forces may be described in a number of ways. For example, a decrease in temperature may induce a relative vacuum thereby creating a convective force. An acoustic force, for example, having one or more oscillating frequencies in a range perhaps between 10 mHz and 100 MHz will often exhibit one or more harmonics (or multiple frequencies). Echoes may result in one or more frequencies that are distinct from the feeder frequency. Geometry and chemical composition of the device may accentuate or dampen frequencies. The acoustic engineer will take into account the importance of such effects when designing the device. A facility for heating the wand may be used to stimulate armpit secretions.

The wand may be set apart or surrounded by a gas porous covering. Such covering will allow gases including VOCs to move from the skin to the sensors. Such gas permeable or porous cover may be perforated open celled plastic material, open celled foam a porous coating, random, stitched, woven, etc. The coating may be selected to absorb out common or problematic molecules to simplify the assay stage. A flushing gas may be used to sweep the skin or clothing and free VOCs for assay. Such gas may be generated chemically, may be heat driven, may be mechanically pulsed, may be provided from a pressurized or compressed gas reservoir, etc. Flushing gas may be alternated with a depressurized stage or a relative vacuum where a small amount of gas is introduced to motivate VOCs followed by a small vacuum to draw the VOCs for NSE analysis. In other embodiments pressurized and vacuum processes are coincident with the offset space forcing movement of gases to collect the VOCs.

The gaseous environment in the present invention is an improvement over prior applications of FET sensing in that the response is both quicker and reversible. Reversibility is critical for high-throughput commercial applications in that it allows for the rapid turnover of samples through avoidance of disassembly and/or cleaning between sample readings. The NSEs on a chip are thus available to assay hundreds or thousands of samples in a day. Reversibility can be accomplished simply by increasing the temperature. Flushing with the ambient gas or another gas can also be used. Continuing to monitor the output signaling from the NSEs provides assurance that the sample has been reversibly cleared and the device is in a mode to accept the next sample.

When the device is so configured, the gases or atmosphere, surrounding the sensors will comprise molecules that interact with NSEs toafter signal generation, transduction and processing-output information relating to the components in the vapor from the sample being examined. Pressure within the NSE chamber is preferably maintained by controllably providing a non-reactive or inert gas. Argon is such a gas often used in manufacture and medical applications, and helium, nitrogen, neon and xenon may also meet the needs of non-reactive or inert applications. Some applications may suggest using a mixture of gases maintained at conditions compatible with testing. For example an extremely light gas such as hydrogen or extremely dense gas such as tungsten hexafluoride may be the only gas used in certain applications or may be admixed to arrive at desired properties, including, but not limited to: acoustic, temperature, reactivity, shielding, polarization, etc. The specific gases used for assaying samples comprise one controllable variable that may be maintained as constant or varied during an individual sample reading.

At least one, but often a plurality of sensor chips, may be included in a device. During use, the sensor chips will be mounted in a controlled atmosphere chamber where vapor phase analyte will be introduced to contact with the sensor chips and thus the NSEs. During analysis, input and output voltages are provided and monitored, respectively, as analyte is delivered to the ambient volume over the chip. Only a vapor phase analyte contacts the NSEs. This provides advantages over many liquid phase SWNT and similar sensors in that sensor size can be reduced without having to account for surface tension, liquid phase excipients are not necessary and turnover rate is not compromised by the requirement to remove the liquid carrier.

Sample Suitability

For medical applications, the analyte sample is most preferably a non-invasive, readily available, biopsied sample, though in some applications a breath or ambient air sample may be collected. The human armpit is a preferred collection owing to its robust circulation and excreting glands. The device may stimulate secretion by providing a warming or heating effect in the collection zone. For example, the device may be warmed before introduction for sampling or may provide a chemical or electrical heating feature to excite secretions. The chemical and/or electrical heating may have an effect of producing a gas to facilitate carrying and delivery of the VOCs for testing. Facilitating gas might also be delivered or provided through a gas delivery tube or pipe; may be sourced from a compressed gas canister; may be inert; may be selected for its interactions with VOCs of interest to improved desired deliveries; etc.

For rapid screening, sweat is an available source for sampling as the apocrine and eccrine glands filter body fluids and secrete water for cooling and odors for recognition and other legacies. These sweat glands generously release metabolic by-products into the armpit area. Thus, information from the entire body is available in sweat.

The device can be configured in several formats. It may be configured as a wand-like device, as a bulbous shape, as a flat, e.g., meter stick, or flat board shaped probe. The device may incorporate sensors with its structure, may connect to a sensor module or may act as a sample collector for delivery to a sensor module. The sensor module may be configured as a sensor/analysis module with computation and/or communication capabilities.

When formatted as an independent sampler, sensor and/or analyzer, the device may be of any shape compatible with the sensing zone or area. For example, within the armpit, the device may be configured as a manageable sized pellet for placement under the arm allowing a lowered arm to confine the device. The device may be in a flattened format like a strip of tape. Multiple devices may be spooled to allow peeling off of a series of devices from a roll. Devices may have a cross-section shaped as disks, oblongs, rectangles, ovals, etc. A height or thickness dimension may be a small fraction, e.g., less than about: 25%, 20%, 15%, 10%, 5%, 3%, 2%, 1%, 0.1%, 05%, 0.01%, etc. The device may be less flattened, e.g., a bulbous, wand, sceptre, cookie or cracker like shape, etc. The containment shell is inert with respect to VOCs. Metals such as steel, titanium, metallic alloys, chloro-fluoro-carbons (CFCs) are preferred low-cost structures or coatings for the sensor body.

Several embodiments may collect and store the VOCs for analysis in another part of the device or in a separate auxiliary device. Several embodiments may incorporate sensing elements and data collection components with data analysis in another part of the device or a separate computation component module. Several embodiments may comprise a sensing module offset from the collection module, wherein the gases may optionally be processed, e.g., by filtering, concentrating, reacting with light or chemical, diluting, chromatographically separating, etc.

In a blood or plasma collection center the device may be used to screen potential donors for suitability. The device has the capability to detect developing pre-symptomatic disease. If a disease is detected, the donor may be excluded from donating on that day. In cases where no doctor is present, the donor may simply be told that an abnormality was seen that may make it unhealthy to donate that day. In some cases a diagnosis may be suggested. The pre-screening can reduce the number of samples that are discarded because chain of analysis of the banked sample indicates it source was from an infected individual. The donation chain benefits from not collecting an unhealthy banked sample but also from avoiding waste of time and collection setups. Blood collection is thus more efficient in collection and storage and safer for the recipients.

Operation of the Device

Pressure differential, released gas, and vibration are examples of available formats for physically stimulating and collecting a sample. Electromagnetic stimulation may comprise visible or non-visible wavelengths. Laser stimulation allows fine control of intensity and targeting, but is only anticipated for use in later generation specialized devices. Physical and/or electromagnetic stimulation may modulate temperature. Once the sample is integrated into the sensing queue, forces including, but not limited to those of: photo momentum, acoustic, gas flow, magnetic, electromagnet, electric, Lorentz force, chip replacement, etc., effects can be used to control movement of compounds within the sample reading area.

Stimulation may be constant, may be ramped or may be paused, pulsed or increased in time or intensity as the analysis requires. Changes may be linear or non-linear, and in practice can be programmed to any desired pattern. Multiple stimulation types may be used in parallel or in series and may be pulsed or varied between types with each type independently controlled. In some analyses, stimulation for a desired time/intensity may be employed to flush, for example, high concentration volatile components, from the sample or to fragment or combine sample constituents.

Sensor Elements on the Chip

A chip may be formed in any desired configuration. For example, a 10×10 sensor array on a chip can provide a compact yet exuberant surface with 100 distinct sensors. Each of these sensors may be configured to optimally detect a single compound or a class of compounds. The functionalization molecules may be different on each chip to adjust specificity and sensitivity. Charge on the chip and temperature are other means of individualizing chip capabilities. During a single sampling session a charge and/or temperature may be modulated to expand the repertoire of the sampling chip. A collection of sensors may be arrayed on a chip in any desirable configuration, e.g., for electronic efficiency, assembly preferences, etc., and/or to align with geometries of the sampling surface or sampling device body.

For example, arrays may be constructed to align with squares or powers of 2 as is common in computation devices and some biological plates. Thus, for some embodiments a 2×2 sensor chip may be sufficient. But more often a greater number of chips will be employed for additional sensitivity and discrimination abilities allowing assay results to be collected on a greater number of analyte chemicals. Thus, a 3×3, 4×4, 5×5, 6×6, 8×8, 10×10, 12×12, 15×15, 16×16, 18×18, 20×20, 25×25, and so on, including intervening squares, mentioned and envisioned here, but not exhaustively incorporated in the text format might be constructed. Other non-square formats are also envisioned. In biology plate sizes based on a power of 2 times 3 are often employed. Thus 48 well, 96, well plates, etc. are common and easily handled by modular software applications. Since binary electronic electronics often increase capacity according to powers of 2, but physical dimensions may not always be supportive of such doubling with each improved version. Software may often be capable of addressing a number in excess of the NSEs on a chip. For example, computations relating to 26 may be used with a 7×7, 8×7, or 50 element chip. A 10×10, i.e., a one-hundred element chip may be served by an application designed for up to 27 (128) element channels. Higher element chips may thus suggest using applications that have capacity for $2^8$, $2^9$, $2^{10}$, $2^{11}$, $2^{12}$, $2^{13}$, $2^{14}$, $2^{15}$, $2^{16}$, $2^{17}$, $2^{18}$, $2^{19}$, $2^{20}$, etc., NSE channels. The chip may be configured with one dimension far in excess of the other. For additional capacity or perhaps to consolidate assay functions in between bulk restoration functions, a chip may be configured in a flexible format in the form of a ribbon with a fraction of the length presented at each analysis function. For example, several 12×8, 10×10, 12×12, 20×20, etc. analytical portions might be exposed with the ribbon being advanced for each subsequent analysis round. A mask may be used to expose only a portion of the chip, for example to select a class or classes of decorations for different exposures to sample VOCs. Such mask may be perforated and movable allowing multiple reads on a portion of the chip without need to restore or advance the chip after each assay or assay condition. A mask with perforations can be made to allow for multiple sensor layers to reside on a chip. For extra high throughput, the ribbon may be advanced in continuous movement where samples are presented at a high rate, perhaps 1/sec if desired. The just used portions of the ribbons may be restored in series with assays by passing through a restoration chamber or may be constructed as an interchangeable or disposable cartridge.

A restoration or cleansing step associated with each analytical round might involve a continuous cartridge or band, where, for example, the assay is accomplished in the assay chamber and when the band is advanced, it passes through another chamber, possibly with a different ambient gas at a different temperature. The chip temperature might not itself be specifically or self-controlled in this format; the ambient gas could provide the thermal energy releasing the assayed compound from the NSE. An atmosphere different from that in the sampling chamber might be used in the restoration phase. Bulk restoration, for example, at the end of a shift might be desired in some circumstances.

The ribbon may be a rigid or semi-rigid strip or might be flexible so as to be compactly spooled. As costs of the NSEs decrease, ribbon formats may be desired and permit disposal after use.

Between subjects, the baton can be restored and refreshed by a blasting or flushing with air or an inert or cleansing gas. For example, the probe or baton may be connected to a gas dispenser that is activated after each subject is tested to blast or stream a steady and strong gas flow. A container, for example in the shape of an umbrella holder may serve as a dip chamber that swirls or otherwise blasts cleansing gas around and through the sensing part of the device.

Then NSEs are preferably extremely compact in size to permit high density and smaller device footprint. NSEs on a chip will be separated from neighbors by insulation barricades. Many insulators are known and can be selected during design based on parameters such as appearance, size, cost, assured availability, etc. Polyamides are common inexpensive insulation barricades. Circuit board material (e.g., FR-4, CEM-1, CEM-3, RF-35, halocarbons, fluorocarbons, Teflon®, PTFE, polyimide, etc.)

Depending on material and anticipated voltages, an inter-element separation of ~50 nano-meters (nm) is often sufficient. Larger voltages may require greater isolation distance. The elements themselves may be any desired shape, e.g., rectangular, rhomboid, hexagonal, triangular, elliptical, circular, irregular, crumpled, creviced, shredded, perforated, layered, masked, etc. Sizes can be miniature, e.g., ~40-50 nm thus suggesting the term nano-sensor. Size is a simple design consideration involving, e.g., manufacturing efficiency, device dimensions, density of sensors, surface to volume ratio of NSE, sensitivity of detection, durability, cost, etc. Accordingly, sizes of elements may be in the area of for example, 40 nm, 50 nm, 75 nm, 100 nm, 200 nm, 250 nm, 500 nm, 0.5 μm, 1 μm, 5 μm, 10 μm, 50 μm, 100 μm. Shapes may be planar, essentially flat on the substrate surface, or at an angle disposed off the surface. Shapes may be irregular, e.g., crumpled or creviced. Shapes may be regular, e.g., hexagonal, creviced, etc. A sensor element disposed on and above a substrate surface may be designed as such to increase or maximize surface area to interact with the vapor that may or may not include a VOC of interest to said sensor.

Although larger elements do not cease to function, the advantages of smaller size generally outweigh advantages attributed to larger element size.

The elements will generally be supported on a non-conductive substrate like Si.

VOCs in Contact with the Chip Sensor Elements

As designed, the NSEs themselves do not contact the sample, only vapor or gaseous phase emissions off the sample are available for contact. Vapor constituents, as the vapor flushes through the sampling chamber, will specifically bind to one or more of the decorations on the NSEs. Depending on temperature and possible gas or combination of gases used as ambient atmosphere, the collated NSE data produce a characteristic response for a specific VOC, combination of VOCs, or class of VOCs. A chip generally will be coated with several types of sensor elements whose sensing specificities are distinguished by having different decorations such as nucleic acids attached on their surface. Polyaromatics and aromatic peptides, including synthetics, may also be valuable decorations. Differential specificity of a chip element may be exhibited at different temperatures, in different atmospheres and/or in different sequence patterns of exposure.

Temperature is significant for at least three important reasons. One: at higher temperatures, the molecules will have higher kinetic energy and thus be less likely to sit docilely on a surface. Different VOC compounds will exhibit different specific temperature effects as will different decorations. Changing the temperature during a sampling session can change specificities and sensitivities. Two: the actual VOC chemical may tautomerize or morph, perhaps with a higher temperature favoring a different bonding structure than a lower temperature. A compound might then, in some embodiments, be detected on different NSEs at different temperatures. Such assay response may be used to more specifically identify and assay a particular compound. Three: improper temperature management can comprise sample integrity, for example, leading to clumping, particulate contamination or other sample degradation. The signature(s) obtained from these analyses may relate to temperature and output signal modulation(s).

One set of embodiments features the sensing apparatus within the wand, bulb or stick format. Analysis may be partially or entirely accomplished in the sensing module with data transferred wirelessly or through a wired interface for further analysis.

A second set features a sensing module physically connected to but offset from the sensing area, e.g., the armpits/axillae. Volatile gas(es) may be flushed through a transfer system that may include sample modifying and/or sorting capabilities. For example, a pressure differential may be used to deliver the sample gases to a sensing chamber/module. This may be an adjunct module in addition to a module at the collection site or may constitute the primary sensing functions. During transport, the sample may pass through filters, dialyzing or chromatographic columns, e.g., to concentrate, reduce background, chemically modify and/or fractionate a sample for downstream analysis. This may add specificity and/or confirmatory data where or when desired.

A third set of embodiments collects and stabilizes the sample(s) into a sample cartridge for remote assay and analysis. This remote sensing/analysis module may share many characteristics of the offset module describe above. When such remote testing chamber procedures are practiced, a sample may be introduced into the testing chamber and maintained therein while a change in temperature alters the sensing specificities of the elements on the chip(s). In embodiments where individual sensors have dedicated temperature controls, NSEs with identical decoration, but read at different temperatures can provide the temperature differentiation analysis more rapidly, i.e., without waiting for a temperature change on the entire chip thus aiding in high throughput analysis.

In general, the interactions between the sensing portions of each sensor and the sensed analyte are low energy bonds or coordination complexes between organic molecules. Bonds do not involve covalent reactions and thus are reversible by changing the conditions in the chamber. Dilution, i.e., simply flushing, in many circumstances will ready the sensor element for its next round. Optionally, a different gas is used for flushing and/or a higher temperature may be used. In addition to thermal or convective restoration processes, any format used to physically move the compounds can be used alone or in concert with others to excite/remove the panoply of complexed VOCs. Forces including, but not limited to those of: photo momentum, acoustic, convective gas flow, magnetic, electromagnet, electric, Lorentz force, chip replacement, etc., effects can be used to prepare for a subsequent sample read. Non-convective restorative forces will be especially advantageous in low pressure, or no added gas embodiments. The broad spectrum of restoration options enables testing of multiple samples types in high throughput operations.

EXAMPLES

On a chip, a simple configuration in binary format comprises an element grid arranged in a 16×16 ($2^4 \times 2^4$) pattern, i.e., 216 ($2^8$) elements. Larger chips generally but not necessarily may follow a continuing binary pattern, i.e., 32×32 (1024 or $2^{10}$), 64×64 (4096 or $2^{12}$), 128×128 (16,384 or $2^{14}$), 256×256 (65,536 or $2^{16}$), etc. A chip may not use all elements as active NSEs. Some may be inactive, some may be held in reserve, some may serve as controls or calibration elements, etc. The chips are functionalized or "decorated" single wall nanotubules (SWNTs). Nucleic acid molecules are inexpensive decorations that can be made with thousands of options. Using non-natural, i.e., nucleic acids not in the human genome or RNA repertoire, many more specificities can be addressed. Amino acids with ringed structures can be incorporated as functional coordinating binders. Thus, specificities of NSEs are tuned to the desired conditions. Sometimes the identical decoration will display different specificity as temperatures change.

A base voltage of generally is in a relatively low, i.e., non-arcing or insulator damaging range for example around 1 pV, but more normally up to 20V, is applied to an input electrode of a sensing element. $10^{-18}$ amp is a minimum amount sensitivity with 0.4 fA being characteristic of our current implementation. The voltage may be static or oscillate (either deterministically or stochastically). Oscillation may include ranging from positive to negative voltages, may include simple on-off switching or other square wave pattern, saw tooth pattern, triangle pattern, stochastic, etc. Voltages may be stepped through a range or introduced in a ramping or cyclic (e.g., sinusoidal) pattern or stochastic perturbation. Voltage may be sent to each sensing element individually or the same voltage may be applied to several sensors, including circumstances where all sensors are fed identical input.

In the NSE, current is or is not delivered from an input electrode to a corresponding output electrode through a field effect transistor carbon layer. In one set of examples the carbon layer is formed as a single walled carbon nanotube (SWNT) layer. In the on mode, the SWNT carbon conducts a current through to an output electrode. When the field effect transistor is in the off mode, the current does not conduct. Several such elements are attached in concert to form a nano-sensor chip. The conductance of the SWNTs on the elemental surface is perturbed by close association with a target compound, for example a volatile organic compound. Binding of such target compound modifies conductance of the SWNTs in such a fashion that the coordination binding acts as a transistor switch turning the gate on or off. In some instances, the coordination will be probabilistic with rapid gating as different portions of the target compound may bind to the SWNT, perhaps at slightly different coordinating atoms. Such probabilistic binding may be temperature or voltage dependent or may vary with the delivering gas. In other instances, the binding may be more constant, simply gating for a range of temperatures/voltages with large zones of on or off signaling.

Specificity

Specificity of coordination is provided by functionalizing or decorating the carbon gate electrode. For example, many sequences of nucleic acid such as DNA or RNA will stringently coordinate or bind with the SWNT structure. These nucleic acids may be naturally occurring or synthetic. The ringed structures of the nucleic acids or other molecules such as peptides containing a large fraction of ringed structures associate strongly with the nanotubular structures. These functionalizing or decorating additions to the SWNTs serve to selectively capture proximal molecules. When the chemical geometry is thus changed, the gating characteristic of the associated carbon bridging the input and output electrodes is modulated. A single element may be associated with a single sequence or a plurality of functionalizing sequences. Output characteristics of gating in response to one or more gaseous compounds, e.g., VOCs are then collated into a data library. When that NSE responds in the same manner, presence of the VOC is confirmed. Stringent selection of element functionalizations, and subsequent application of the controllable assay variables can optimize certainty of VOC identification at a desired level, for example, increasing manipulation of the variable parameters can achieve certainty of 99+%. In special circumstances, for example to develop rapid profiling of a new VOC signature (i.e., pathogen), a simplified screening protocol or developmental process may begin with a lower level of certainty, e.g., 85%, 95%, etc. Subsequent refinements then could be applied to raise the level of certainty until reaching a mathematical and chemical sensitivity to an acceptable level, e.g., a 99+% certainty.

A single element may be capable of indicating the presence of more than one compound. For example, similar compounds may not be distinguished in their association/coordination with the element surface and therefore may in certain circumstances produce indistinguishable signals on their own. But the single element may, for example, in conjunction with one or more other elements provide definitive results with respect to the VOCs that may interact with any one element. Alternatively, the single element when operated at a different temperature, voltage or other variable may distinguish between the different compounds binding the element under static conditions. The discussion above describing the variable inputs and input patterns and different resulting outputs relates to such differentiation capabilities.

Fast Tracked Testing and Reading

One embodiment may include a simplified assay, perhaps featuring a chip with fewer component element or element types than a mass screening formatted chip, e.g., using only a fraction of the DNA species on the general use chip. In simplified embodiments fewer parameters may be manipulated, perhaps a static system where one or more variables, such as, voltage, temperature, etc. have a reduced range or remain constant. When AI identifies, for example, a simplified signature for a specific set of diseases or a specific disease, such as a new virus or strain of virus, the device may be instructed to operate in a simple detection mode similar to that of a +/− strip test. Chips may thus be made specific for different preferred assays or a regular chip may be used with simplified readings. Such configurations may be used, for example to screen for specific traits that may indicate individuals at risk or not at risk or may be used as a confirmatory test indicative of a prior result, positive or negative. Chips may incorporate a selection of sensing elements that will serve in self calibration.

A simplified data analysis may be inherent in the chip whether at the collection site, offset from the collection site or remote. For example, a circuit can be built with specific sensors in series and/or in parallel. When the circuit produces the right gating, a positive result would be output. A side circuit on the chip possibly sharing portions of the positive negative circuitry may be included as a control. In some embodiments a completed control circuit with an incomplete or open positive circuit may produce a "negative" signal. The chip itself may be individualized to contain a coded instruction for the machine to operate in the designated mode, e.g., an optical patch, physically slotting, an RFID, actual machine readable code, etc., may instruct the machine to operate in the preferred program manner. Such a streamlined approach can enable extremely high throughput analysis of targeted profiles.

Shielding

As sensitivity is heightened, machine stability becomes more important. Therefore, depending on output sensitivity targets, formats of samples, formats of delivering the samples, etc., shielding is considered a major design consideration. For example, if acoustics are used to advance, modify, present, or to remove samples, acoustic shielding in the relevant wavelengths and consideration of harmonics of the structural hardware, should be taken into account during design and installation. Passive, e.g., sound insulation, or active, e.g., sound cancellation shieldings are compatible with such shielding requirements. Electromagnetic shielding can be any suitable format, e.g., conductive material such as copper, nickel, mu-metal, amorphous metal, conductive plastics, conductive paints/inks, etc. In general, the device should be protected or shielded from any influences, that interfere with performance including, but not limited to: acoustic, temperature/thermal, electromagnetic, visible, infrared, ultraviolet, radio/micro waves, magnetic, electric, etc. For particular environments, including, but not limited to: space travel, zero or low gravity, proximity severe weather events, deep sea or deep underground, high altitude, atmosphere, where the device is to be used, additional shielding, e.g., from heat, ultraviolet light, solar wind, ionizing radiation, high velocity transit, constrained environments, densely populated locations, proximity to nuclear power plants or engines, vibration, etc., is a desired design feature. While general ambient conditions for most of the device's intended uses will be relatively standard. When a device is designed for use in any extreme environment, additional relevant shieldings should be studied and applied where appropriate for example when designed for use for a long duration space flight.

Data Storage and Analysis

Raw data may be stored in a library linked to the sample source with any other relevant information including, but not limited to: disease diagnosed, disease status, nourishment history, time of collection, volume of sample, volume analyzed, medical history, preparation steps before analysis, storage and/or chain of custody conditions, medications, gender, age, etc. Such library may be stored or transmitted in any available format and process taking safety, privacy, consent, cost, relevant laws, legal jurisdiction, storage density, transit speed, etc. into account with a goal of interfacing groups of machines in a knowledge base where each device teaches and learns from others. Portions of the library may be stored in diverse locations including any available format, e.g., single encrypted, double encrypted, or block-chain coded.

Files in such library may be compiled and analyzed by knowledgeable humans, but more preferably using machine learning and/or artificial intelligence in any combination. Such processing, analysis and comparing multiple samples with associated information will then be useful for continuous expansion of the disease repertoire and the improvement of diagnostic accuracy and quality of the output data.

Handheld Rapid Scanner

A scanner may be configured as handheld sensor for rapid scanning. An exemplary device may feature two parallel sensing chips. Such parallel chips may be separated by a barricade, e.g., a thin plastic sheet in the middle of a flow chamber. For example, sensing chips on the extremes or on the central barricade having $2^4$, $2^5$, $2^6$, $2^7$, $2^8$, $2^9$, $2^{10}$, or more, or e.g., squares of other integers depending on design convenience may receive flowing samples (generally air). Chips may be on both the walls and the separating chip. An exhaust fan renders a negative pressure to provide suction to other openings in the unit. An input cone or funnel, when open, serves to collect ambient air from near the opening. Alternatively, the suction may switch on or off or be gated distal to the opening and thereby serve to initiate the air collection incorporating the sample gases. Depending on the path length and resistance to flow the exhaust rate will be adjusted to control flow rate. Linear flow rate across a chip is not critical for sensor operations. Sampling time and sensitivity are factors to be considered in selecting an operational flow rate. For example an optimal linear rate for many operations will be selected from a range of about 0.02 to 6.0 $cm \cdot sec^{-1}$ including, but not limited to: about 0.02, 0.025, 0.03, 0.035, 0.04, 0.045, 0.05, 0.055, 0.06, 0.065, 0.07, 0.075, 0.08, 0.085, 0.09, 0.095, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0 $cm \cdot sec^{-1}$, etc. When different flows are desired between channels, channel resistance may be separately adjusted to control flows across the chips.

Stochastic or pulsed flows may be gated across the unit or individually in each sensing channel. Total flows may be essentially constant when the gating serves to switch flows between the sensing chambers. A disposable cap may be employed to prevent accidental contact of the unit with the subject. When special sampling control is desired the cap may serve as a measuring spacer to make sensing distance between the unit and the subject repeatable.

As a picture example, two 256 element chips are disposed in parallel along a flow path. A separating barricade allows for separation between channels. In this example, the left sample is taken from between an inch or two above the skin; the right sample is taken from a more distal port facing away from the subject. The parallel sampling allows the analytical software to distinguish between ambient environment and subject VOCs. An exhaust fan provides a flow rate of 1 $cm \cdot sec^{-1}$ across a 1.7 cm chip. Sampling time of about six seconds provides sufficient flow to deliver sample VOCs across the chips for analysis.

The device is placed in a filtered chamber or is removed from proximity to potential subjects as flow continues. This continued flow serves to cleanse or flush the chips in preparation for the next subject sample.

In preferred embodiments the flow across the chips proceeds into an exhausting chamber or path which may provide heat and/or ultraviolet radiation for inactivating potentially infectious particles associated with the sampling. Filtration, e.g, using a HEPA filter may replace exhaust treatment or may serve to augment it.

The sensors in this embodiment are tuned for the sigma3 virus (an arbitrary disease of interest). When a sigma 3 VOC signature is not evident, a green LED flashes to indicate good-to-go. An orange or blue light may suggest a retest or a test using another protocol. When a sigma 3 VOC signature is evident, a red LED flashes to indicate an undesired or unacceptable result. The subject may be sequestered or otherwise prevented from interaction with other individuals. Sound alerts may accompany the visual signals or may serve as alternates.

The device may be configured to test for a single factor like a disease of particular interest at that time or place. Chips may be configured to test for a plurality of events with letter codes, numeric codes, voice or other indications. Additional chips may modularly be placed in sequence or parallel to assay for a second or third, or other outcome of interest.

Early Warning System

One especially poignant application of this device and technology relates to infection by a virus. Viruses are often specific to a small population of cell types at a particular state of development. For example, in the case of a corona virus such as the SARS-CoV-2 virus that is responsible for the COVID-19 pandemic, the "spike" or S-protein binds to Angiotensin-Converting Enzyme 2 (ACE2) found on human cells. The spike protein also acts in conjunction with another cell surface protein, TMPRSS2, to initiate cell processes causing viral entry. ACE2 is found on multiple cell types in the human body, including, but not limited to: endothelial cells of the circulatory system, enterocytes of the small intestine an in especially high numbers on Type II alveolar cells in the lung. Type II cells are the cells that secrete surfactant coating the air sac surfaces. Surfactant lowers the surface tension of the fluid coating the alveoli and thus helps to keep air sacs in an open, rather than a collapsed state. When the alveolar cells are targeted and eventually killed to release new virus, breathing becomes more difficult as the air sacs lose air exchange surface area and increase amount of fluid in the lung. This diminished lung function can be diminished further as the immune system gears up to fight off the virus. The immune responses can further fill lungs with fluid and pus and severely compromise breathing. In this example, the type II cells are known for high contents of dipalmitoylphosphatidylcholine, ethanolamine, cholesterol and many trace organics.

Certain adaptations of ACE2 bearing cells resulting to their adaptations to stresses from obesity, renal disease, cardiac stress, etc. apparently makes these cells better targets for the virus. Lung cells die in high numbers and release contents upon cell lysis and death. Some content is expired in the breath, but most is transported by the blood for processing and removal. Similarly, when the blood is filtered by the kidneys, VOCS released during cell lysis will be delivered into the urine. When passing through the glands of the armpits the VOCs are released essentially undiluted as they would be in plasma or urine. As one example, the appearance of VOCs in patterns relating to a type II cell origination provides evidence of attack on these cells. Metabolic products will be carried through the circulatory system providing access throughout the body including axillae. Knowing which pathogens are in circulation can increase the certainty that the source is from the SARS-CoV-2 actively pandemic virus. The human, artificial intelligence, and/or machine learning can be more certain when more information is available. For example, persons with the adapted and compromised cells mentioned above will also exhibit breakdown products from these cells in their sweat. Assays indicating breakdown products from the non-lung compromised cells can provide stronger certainty that the SARS-CoV-2 is the actual culprit.

Identification of Emerging Bio-threats

However, even before a virus is identified, distinct patterns associated with an unknown disease may appear in several samples and be concentrated in one or more locations. This information may help to characterize or identify the unknown pathogen because, when cells are attacked and become infected, they start producing and releasing abnormal VOCs and abnormal levels of other VOCs characteristic of the cell type. Therefore, a network of devices deployed in hospitals (and military installations, factories, airports, laboratories, points of entry, etc.) can act as an early warning system of new emerging viral threats whether natural on man-made. A network and early warning system such as the one described herein can rapidly identify and provide a VOC profile of the new pathogen suitable for use in identification of healthy or infected individuals even before genetically decoded and named.

The present invention eliminates the need for genetic decoding testing and development, manufacture and distribution of new testing kits. The device of the present invention does not require special chemical analytical reagents or specially trained laboratory personnel and can be self-administered. When the preferred analyte, sweat, is used, only minimal chemical or biolab protective gear is necessary. Therefore, massive scalable testing is enabled using sweat (a non-invasively accessible sample).

Each active infective virus will induce specialized responses in the target cell thereby producing a signature pattern of cell metabolism that results in a VOC population highly associatable with the specific virus, sometimes even a specific strain of virus. Each virus requires a receptive cell to endocytose the viral genome and generate copies of new virus. To gain access the virus must bind to a particular portion on a cell. Viruses are thus unique in the cell type or cells types they attack. The pattern of cells and the responses to the attack will be unique to each new virus. So when devices of the invention are interfaced with each other and share data, an early warning wake-up call can identify a potential health risk long before it becomes a crisis or would be recognized following current practice. Through relation to previous data, the algorithms can identify the targeted cells and therefore potential anomalies and treatments related to the cells under attack.

Containment of Emerging Bio-Threats

Axillary samples assayed using the present device can deliver a unique signature profile associated with the viral infection within seconds or minutes of sample introduction. Because the eccrine and apocrine systems filter blood that has traveled through all body organs, the sweat and emitted VOCs contain metabolic products produced in each organ and therefore will contain VOCs characteristic of the cells under attack. This can help to identify the pathogen in some circumstances, but with new pathogens, by identifying the cells that the viruses use for replication can suggest who is at greater risk and can help in rapidly developing treatment protocols. The rapid identification and recognition of an emerging bio-threat combined with massive scalable testing as provided for in the present (networked) invention will enable rapid containment of a geographically designated containment zone greatly reducing the virus' ability to continue its transmission.

Assays under the present invention can recognize a new appearance of previously known signatures or appearance of a previously unknown signature. Geographic location, possibly to a single town, lab, hospital, metropolitan area, zip code etc., will allow instant designation of proposed containment zones. In these zones, rapid testing of associated individuals and contact tracing where relevant can be initiated and accomplished before the numbers of afflicted persons become burdensome or overwhelming. An outbreak, even from a previously unknown pathogen, can therefore be identified and stopped long before reaching epidemic status and hence prevent an epidemic event expanding into a pandemic. In conjunction with the identification and partitioned follow-up of the disease making a first appearance, the disease can be characterized as to source, afflicted cells, possible treatments and/or preventions, etc. Depending on the size and population (and density) of the containment zone, the device of the present invention is modularized to achieve massive scalability from a single unit having a capacity to assay ~500 samples/day to a modularized assortment of networked units with capacity in excess of 1,000,000/day. Rapid deployment to meet the needs of a nationwide emergency or to relieve local infrastructure from being overwhelmed during surge demand is available using prefabricated high throughput assay laboratories outfitted with devices and automated sample management facilities. These automated self-contained VOC assay factories are designed and built to be transportable e.g., using standard e.g., ISO sized shipping containers (e.g., 20 or 40 ft, HQ or normal height.). Each of the prefabricated facilities can be deployed using normal transport, e.g., rail, truck, boat, cargo plane or helicopter, to a location in need. The container, depending on circumstance, can be equipped with an electrical generator and supplied with a dedicated accompanying fuel source to supply the generator when warranted, for example, in disaster circumstances. However, the preferred embodiment is to be delivered to and actuated to meet surge demand, for example at a postal facility, a parking lot, a stadium, an open field, on the back of a trailer truck, etc., i.e., wherever is advantageous for optimizing throughput.

In a repeated test, a decrease in viral disease signature may be taken as a sign that the host has or has not resolved the infection.

Cancer

The systems of the present invention are ideally suited for detecting, diagnosing and evaluating cancers in general and specific cancers. Cancers do not involve all the cells in the body but originate within a specific cell population. As the metabolic activity in the cancer cells is altered, their VOC production changes. Some metabolic changes are common to many cancers. So in some embodiments a signature may be taken as indication of a class of cancers, e.g., epithelial cell cancer. But as signature information is refined the evidence appears to show that even different breast cancers can be distinguished. It is well known that some cancers' responses to hormones if different from other cancers.

Conventional monitoring of cancer progression to aid in diagnosing timing for possible surgical, chemical or thermal intervention is embodied for example in the PSA test associated with prostate cancer. Such urinalysis samples can be put to braoder use when presented to the NSEs of the inventive devices. Such group and/or population comparisons or time course within an individual are similarly applicable in embodiments of the present invention. Similar cancer test markers, including, but not limited to radiographic imaging and biosampling, e.g., tissue biopsy, blood, urine, etc., may be used in conjunction with the present invention on individual or group-population data.

Grouped data might be applied in setting standards or crafting algorithms for setting cancer screening protocols and reported results. Such broad-based historical data may similarly be applied in the monitoring of an individual's cancer progressions and/or course of treatment. Risk factor analyses may also be included in assessing relevance and weights to be applied to various data points or sets.

Depending on treatment regimens and cancer types timed assessments of an individual's cancer status may be early, e.g., within a day or several days, but may be more informative if assessments are made longer term, e.g., weekly, monthly, quarterly, annually, before each treatment or a number of treatments, during treatment, shortly following treatment, etc.

Autoimmune Disease

There is evidence to support that many autoimmune diseases are suitable target for analysis using systems of this invention. In general, a signature immune response underlies the autoimmune cascade. When the attacked cells respond, their metabolisms are particular to the attacked cell type, cell age, location and the like. The specialized metabolisms of the altered cells will produce their particular signature VOC outputs. Thus, VOC analysis in accordance with this invention will be expected to assist in diagnosing various autoimmune diseases.

Embodiments

Embodiments include devices comprising a plurality of NSEs configured in a detecting cartridge; with a detecting cartridge optimized for a preselected disease or condition or a preselected group of diseases or conditions and/or a detecting cartridge selected for detecting a plurality of diseases of conditions; with at least one disease determined by a blood banking authority; and devices that may have a surface area designed to interface with a human axilla.

Embodiments may also feature two contact areas on opposing surfaces of said module; devices shaped as a cylinder that may have a circular cross section; an ovular cross section may be with a flattened curved shape or a conical shape.

Microbiome

Another exemplary application is understanding of a person's microbiome. Surface microbes generally emit only trace amounts of VOCs and thus are not yet prime targets for analysis. But ambient gases surrounding an organism may be analyzed to obtain signature information emitted from the sample, whether from the organism or its associated microbiome. In a related set of analyses, since the gut microbiome directly feeds into the bloodstream for filtration by the kidneys this information can be more concentrated and provide a stronger signal. VOCs produced by the organism and the gut microbiome will therefore be present in general analysis. Thus, this microbiome status can be monitored in accordance with the present invention.

In another embodiment, a FET or similar sensor system as known in the art to assay components in a liquid phase may be associated with the vapor phase analysis of the present invention. Large biomolecules such as proteins are not found in VOC off-gas. Assays of antibody and many antigenic larger molecules can add to the assay information obtained using the base system of the present invention. Such information, especially IgM or lgG status can help delineate a patient's historical experience with a disease. Such information can also be helpful in determining the efficacy of immunizations and/or the frequency of recommended booster immunizations. SWNT-based biosensor diagnostic devices in contact with an analyte containing liquid have emerged the current millennium as effective high sensitivity detectors for medical, industrial, environmental, toxicological, quality control, pharmaceutical development, etc., applications. Neutral and ionic compounds in aqueous solutions including, but not limited to: insulin, human chorionic gonadotropin, human growth hormone, prolactin, glucose, fructose, galactose, hormones, neurotransmitters, drugs, amino acids, peptides, proteins, products of micro-organisms—including pathogens and microbiome members, cancer indicative nucleic acids and proteins, etc. have been investigated using such technologies. In a recent review article, electrical, optical, electrochemical, outputs were characterized as sensed signals. Szunerits, S., & Boukherroub, R. (2018). Graphene-based biosensors. Interface focus, 8 (3), 20160132. https:/-/doi.org/10.1098/rsfs.2016.0132. Optical properties include light transmission (transparency), light changing (fluorescence), reflecting, and absorbing properties of graphene in various formats. Antigen-antibody complexes are detectable.

Such add-on device could be advantageous when the presence of a large (non-volatile) molecule might be important information. Accordingly, an embodiment of the present invention may incorporate a liquid phase detection component to augment data obtained in the vapor phase.

As an illustrative example of a multi-analysis device, would be one in which two or more types of chips are used. The first type of chip is that of the base device described above to produce the VOC signature. The second type is a chip that analyzes a wet or liquid phase sample. While many alternative form factors may be used, a cartridge (e.g., containing a liquid to off gas the vapors for assay by the first chip) can be configured to incorporate a second type chip that includes sensors for e.g., viral nucleic acid, antigen and or antibodies or other non-volatile compounds of interest. Other configurations may optionally deliver samples to such a liquid phase analysis chip in parallel to delivering vapors to the gas phase sensors. Thus, data from multi-analysis procedures on the same sample can be collated and analyzed together.

Another illustrative example embodies a relatively large protein attached to or in close proximity to the liquid-based NSE(s). Such protein may be a protein with affinity for the molecule in question. When binding said molecule and thus changing its 3-D structure a signal can result in detection of the molecule in question. Such sensor component might be selected to provide immune status, e.g., presence of one or more classes of antibodies or target of the antibody. Enzymes, hormones, hormone receptors, neuro-active compounds and receptors are examples of large molecules or proteins that might be assayed in such liquid phase analysis. In some embodiments of the invention the liquid phase and vapor phase may be assaying different components of the same event, such as an antibody active in the lung that might bind SARS-CoV-2 or the liquid phase sensor might sense a VOC that can be assayed in the vapor phase thereby helping to increase confidence in this dual phase multi-analytical system is an advance over existing systems in that it provides, from a single sample, a detailed understanding of an individual's health status.

The invention claimed is:

1. An analytical device comprising a detector unit capable of interfacing with an analytical unit, said detector unit physically aligned with a container presenting a liquid sample; said alignment comprising a path through which Volatile Organic Compounds (VOC(s)) traverse from said presenting container to said detector unit; said detector unit comprising a module designed to collect a vapor phase sample for delivery to a plurality of detection surfaces capable of interacting with said vapor phase; said detection surface comprising a nano-sensor element (NSE) layer between an input and an output; said input in contact with a base power source; said output in communication with at least one data collector; said NSE layer associated with a selection component with selection specificity for one or more compounds of interest; said selection component when in contact with or in close proximity to a VOC compound present in said vapor phase selectively altering a signal to said output; and a component for collecting said signal from said output and presenting said signal to an analytic component.

2. The device of claim 1 wherein said selection specificity comprises at least one of an attractive component and a repulsive component.

3. The device of claim 1 further comprising an electronic module that analyses and processes signal from said output to produce a sample profile, and an interface that compares said profile to at least one signature in a signature library.

4. The device of claim 3 wherein said interface further comprises a receiving module that produces a report of signatures that match said sample profile.

5. The device of claim 1 wherein said presenting container is configured to contain a urine sample.

6. The device of claim 1 comprising a gas selective permeable membrane for isolating said vapor phase sample.

7. The device of claim 1 wherein said sample zone whose pressure is relatively negative in comparison to an ambient pressure.

8. The device of claim 1 further comprising a heat source for warming the sample zone.

9. The device of claim 1 further comprising a feature that exhausts gas into the sample zone thereby providing a collectible volume of gas carrying said VOCs.

10. The device of claim 9 wherein said exhausted gas comprises an inert gas.

11. The device of claim 1 wherein said NSE layer comprises a carbon.

12. The device of claim 11 wherein said NSE layer is decorated with a nucleic acid.

13. The device of claim 12 wherein said nucleic acid comprises a polymer of about eight to about sixteen bases.

14. The device of claim 12 wherein said nucleic acid comprises a DNA.

15. The device of claim 12 comprising an array of NSEs, said array comprising groups of NSEs, said groups distinguished by at least one characteristic selected from the group consisting of: at least a first decoration distinct from at least a second decoration, at least a first temperature distinct from at least a second temperature, and at least a first base voltage distinct from at least a second base voltage.

16. A device of claim 15 comprising at least a first decoration optimized through chemical analysis of at least one VOC to more specifically or more robustly interact with said at least one VOC.

17. The device of claim 1 further comprising at least one physical component that shields the detector unit from undesired physical effects.

18. The device of claim 17 wherein said physical component that shields comprises a shielding component selected from the group consisting of: acoustic shielding, temperature/thermal shielding, electromagnetic shielding, visible light shielding, infrared light shielding, ultraviolet light shielding, radio/micro wave shielding, magnetic shielding, electric shielding, vibration shielding and unauthorized use shielding.

19. The device of claim 18 comprising at least one conductive material selected from the group consisting of: copper, nickel, mu-metal, amorphous metal, conductive plastics, conductive paints and conductive inks.

20. The device of claim 19 wherein at least one molecule in the vapor phase has its position under control of at least one force selected from the group consisting of: photo momentum, acoustic, convective gas flow, magnetic, electromagnet, electric, and Lorentz force.

* * * * *